United States Patent [19]
Hintz

[11] Patent Number: 5,381,783
[45] Date of Patent: Jan. 17, 1995

[54] MOUTHPIECE WITH A BREATHING CHANNEL

[76] Inventor: Roger L. Hintz, P.O. Box 51, Eldorado, Wis. 54932

[21] Appl. No.: 175,248

[22] Filed: Dec. 29, 1993

[51] Int. Cl.6 .................................................. A62B 18/08
[52] U.S. Cl. ................................ 128/206.29; 128/861
[58] Field of Search ............... 128/201.11, 206.29, 128/848, 859, 860, 861

[56] References Cited

U.S. PATENT DOCUMENTS

| | | | |
|---|---|---|---|
| Re. 33,442 | 11/1990 | George | 128/860 |
| 1,146,264 | 7/1915 | Kelly | 128/861 |
| 1,674,336 | 6/1928 | King | 128/861 |
| 2,459,273 | 1/1949 | Freedland | 128/861 |
| 2,521,084 | 9/1950 | Oberto | 128/206.29 |
| 2,708,931 | 5/1955 | Freedland | 128/861 |
| 3,217,708 | 11/1965 | Roberts | 128/861 |
| 4,305,709 | 12/1981 | Bruhn et al. | 128/861 |
| 4,664,109 | 5/1987 | Rasocha | 128/861 |
| 4,862,903 | 9/1989 | Campbell | 128/861 |
| 5,003,994 | 4/1991 | Cook | 128/848 |
| 5,074,295 | 12/1991 | Willis | 128/200.24 |
| 5,092,346 | 3/1992 | Hays et al. | 128/848 |
| 5,117,816 | 6/1992 | Shapiro et al. | 128/200.24 |
| 5,165,423 | 11/1992 | Fowler et al. | 128/861 |

FOREIGN PATENT DOCUMENTS

| | | | |
|---|---|---|---|
| 2320501 | 11/1974 | Germany | 128/848 |
| 698570 | 10/1953 | United Kingdom | 128/861 |
| 874480 | 8/1961 | United Kingdom | 128/848 |

*Primary Examiner*—Edgar S. Burr
*Assistant Examiner*—Aaron J. Lewis

[57] ABSTRACT

A new and improved mouthpiece apparatus which includes a breathing channel, wherein the apparatus includes a first wedge portion for wedging between top teeth and bottom teeth of a first side of a wearer's mouth. A second wedge portion is provided for wedging between top teeth and bottom teeth of a second side of a wearer's mouth, and a bridge member connects the first wedge portion to the second wedge portion. The first wedge portion and the second wedge portion lie in a common plane, and the bridge member projects upward from the common plane, such that a wearer's tongue can be located under the bridge member in a natural resting position.

2 Claims, 1 Drawing Sheet

MOUTHPIECE WITH A BREATHING CHANNEL

BACKGROUND OF THE INVENTION

1. Field of the Invention

The present invention relates generally to mouthpieces, and, more particularly, to mouthpieces that include air flow channels that permit breathing through the mouthpiece.

2. Description of the Prior Art

Mouthpieces are well known in the art for a number of purposes. Mouthpieces worn by athletes are used to protect teeth and gums from mechanical force. Mouthpieces worn by underwater swimmers are used to permit air flow to a person's lungs when the person is underwater. Some mouthpieces are to be worn by persons who are sleeping to prevent snoring. For example, the following U.S. patents disclose a number of mouthpieces that have been developed over the years: U.S. Pat. Nos. 4,862,903; 5,003,994; 5,074,295; 5,092,346; and 5,117,816.

More specifically, U.S. Pat. No. 4,862,903 discloses a mouthpiece used by an underwater swimmer. An air channel is provided, and a portion of the mouthpiece receives the wearer's teeth for retaining the mouthpiece in the mouth. However, when this mouthpiece is worn, the wearer's tongue must be moved from its natural position in the mouth. In this respect, it would be desirable if a mouthpiece were provided which permitted a wearer's tongue to be maintained in its natural position in the mouth when the mouthpiece was worn.

U.S. Pat. No. 5,003,994 discloses a mouthpiece that is worn when a person is sleeping to prevent snoring. An upper portion is positioned with respect to a lower portion so that the jaw is shifted during sleep. This helps prevent snoring. When a mouthpiece is worn by a wearer during normal awake conditions, the shifting of the jaw to an unnatural position may not be desirable. In this respect, it would be desirable if a mouthpiece were provided which did not shift the jaw to an unnatural position when the mouthpiece is in use.

U.S. Pat. No. 5,074,295 discloses a mouth-held holder that is used for holding a mouth-held implement. A socket is provided at one end of the mouthpiece for receiving the mouth-held implement. The additional components relating to the socket are totally superfluous in a mouthpiece that is not used to support a mouth-held implement. In this respect, it would be desirable if a mouthpiece were provided which did not include superfluous components for connecting to mouth-held implements.

U.S. Pat. No. 5,092,346 discloses a mouthpiece to be worn by a person at night to prevent snoring. With this device, a cam is used to shift the lower jaw to a more forward position than is natural. As mentioned above, it would be desirable if a mouthpiece did not move the jaw into an unnatural position.

U.S. Pat. No. 5,117,816 discloses a mouthpiece that is used to prevent snoring. The mouthpiece has a handle that is used to position the mouthpiece properly in the mouth. The additional costs and complexities in using a handle for the mouthpiece are undesirable. In this respect, it would be desirable if a mouthpiece were provided which does not include a handle for positioning the mouthpiece in the mouth.

Still other features would be desirable in a mouthpiece which includes a breathing channel. For example, when a mouthpiece is placed in a mouth, it is generally held in place by the wearer's teeth, both upper and lower teeth. The shapes and sizes of people's teeth vary considerably. Therefore, it would be desirable if a mouthpiece could be fitted to the respective shapes and sizes of a wearer's teeth.

There is a certain circumstance when a mouthpiece would be desirable but is not presently used. When a person has a computer assisted tomography (CAT) scan of the head, the person is asked to lay flat on his stomach and have the chin rest in a pad. The person is asked to stay absolutely still for twenty minutes. For a person who cannot breathe through the nose, the mouth would have to opened slightly to permit adequate breathing. However, after a relatively short time, it becomes quite difficult for a person to be absolutely still while maintaining the mouth slightly opened with the chin resting on the pad. The jaw muscles become rapidly strained, and in their strained condition, they may tend to move, shake, or waiver. The consequence of not remaining adequately still is to repeat the expensive test and run the risk of failing to keep adequately still the next time. An appropriate mouthpiece would afford the person the opportunity to allow the lower jaw to be pressed up against the upper jaw without straining jaw muscles and without causing head movement.

Thus, while the foregoing body of prior art indicates it to be well known to use mouthpieces, the prior art described above does not teach or suggest a mouthpiece with a breathing channel which has the following combination of desirable features: (1) permits a wearer's tongue to be maintained in its natural position in the mouth when the mouthpiece is worn; (2) does not shift the jaw to an unnatural position when the mouthpiece is in use; (3) does not include superfluous components for connecting to mouth-held implements; (4) does not include a handle for positioning the mouthpiece in the mouth; (5) can be fitted to the respective shapes and sizes of a wearer's teeth; and (6) affords a wearer an opportunity to allow the lower jaw to be pressed up against the upper jaw without straining jaw muscles and without causing head movement. The foregoing desired characteristics are provided by the unique mouthpiece with a breathing channel of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved mouthpiece apparatus which includes a breathing channel wherein the apparatus includes a first wedge portion for wedging between top teeth and bottom teeth of a first side of a wearer's mouth. A second wedge portion is provided for wedging between top teeth and bottom teeth of a second side of a wearer's mouth, and a bridge member connects the first wedge portion to the second wedge portion. The first wedge portion and the second wedge portion lie in a common plane, and the bridge member projects outward from the common plane. More specifically, the bridge member projects upward from the common plane such that a wearer's tongue can be located under the bridge member in a natural resting position. If desired, the entire apparatus can be made from inexpensive plastic and be disposable.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved mouthpiece with a breathing channel which has all of the advantages of the prior art and none of the disadvantages.

It is another object of the present invention to provide a new and improved mouthpiece with a breathing channel which may be easily and efficiently manufactured and marketed.

It is a further object of the present invention to provide a new and improved mouthpiece with a breathing channel which is of durable and reliable construction.

An even further object of the present invention is to provide a new and improved mouthpiece with a breathing channel which is susceptible of a low cost of manufacture with regard to both materials and labor, and which accordingly is then susceptible of low prices of sale to the consuming public, thereby making such mouthpiece with a breathing channel available to the buying public.

Still yet a further object of the present invention is to provide a new and improved mouthpiece with a breathing channel which permits a wearer's tongue to be maintained in its natural position in the mouth when the mouthpiece is worn.

Still another object of the present invention is to provide a new and improved mouthpiece with a breathing channel that does not shift the jaw to an unnatural position when the mouthpiece is in use.

Yet another object of the present invention is to provide a new and improved mouthpiece with a breathing channel which does not include superfluous components for connecting to mouth-held implements.

Even another object of the present invention is to provide a new and improved mouthpiece with a breathing channel that does not include a handle for positioning the mouthpiece in the mouth.

Still a further object of the present invention is to provide a new and improved mouthpiece with a breathing channel which can be fitted to the respective shapes and sizes of a wearer's teeth.

Still a further object of the present invention is to provide a new and improved mouthpiece with a breathing channel which affords a wearer an opportunity to allow the lower jaw to be pressed up against the upper jaw without straining jaw muscles and without causing head movement.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

With reference to the drawings, a new and improved mouthpiece with a breathing channel embodying the principles and concepts of the present invention will be described.

Figure 1:
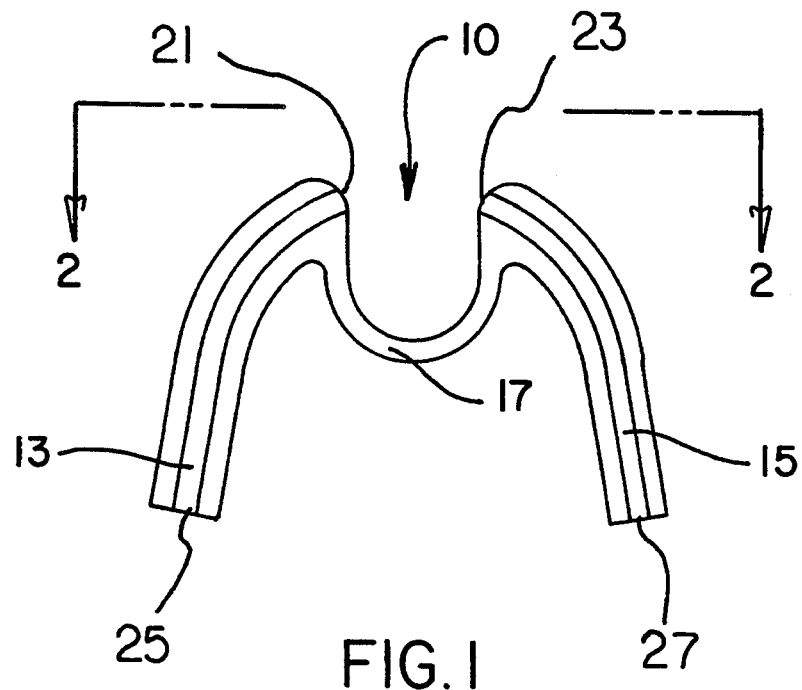
FIG. 1 is a top view showing a preferred embodiment of the mouthpiece with a breathing channel of the invention.
Figure 2:
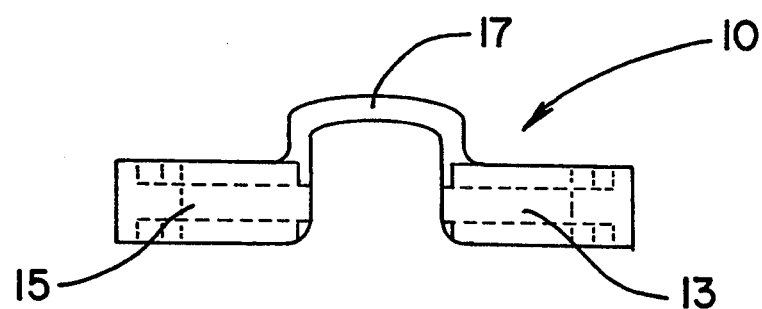
FIG. 2 is a front view of the embodiment of the mouthpiece with a breathing channel of the invention shown in FIG. 1.
Figure 3:
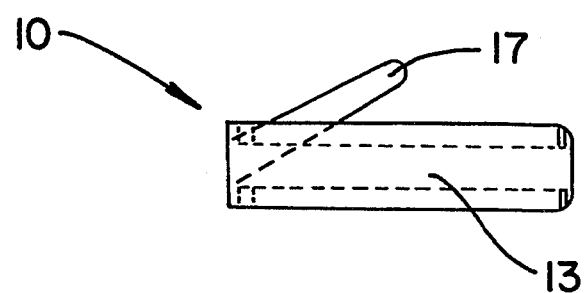
FIG. 3 is a side view of the embodiment of the invention shown in FIGS. 1 and 2.

Turning to FIGS. 1-3, there is shown an exemplary embodiment of the mouthpiece with a breathing channel of the invention generally designated by reference numeral 10. The mouthpiece with a breathing channel 10 includes a first wedge portion 13 for wedging between top teeth and bottom teeth of a first side of a wearer's mouth. A second wedge portion 15 is provided for wedging between top teeth and bottom teeth of a second side of a wearer's mouth, and a bridge member 17 connects the first wedge portion 13 to the second wedge portion 15. The first wedge portion 13 and the second wedge portion 15 are shown as approximately quarter-circular structures so that the overall profile of the combination of the first wedge portion 13, the bridge member 17, and the second wedge portion 15 is semi-circular. The first wedge portion 13 includes a proximal end 21 and a distal end 25. The second wedge portion 15 includes a proximal end 23 and a distal end 27. In the Figures, the bridge member 17 is an inverted U-shaped rod structure in which one end of the U- shaped structure is connected to the proximal end 21 of the first wedge portion 13, and the second end of the U-shaped structure is connected to the proximal end 23 of the second wedge portion 15. The first wedge portion 13 and the second wedge portion 15 lie in a common plane, and the bridge member 17 projects upward from the common plane and toward the distal ends of the wedge portions, such that a wearer's tongue can be located under the bridge member 17.

In use, a person opens one's mouth and places the mouthpiece of the invention between the top and bottom teeth. Then, the person attempts to close the mouth upon the mouthpiece. The wedging action of the first wedge portion 13 and the second wedge portion 15 between the top and bottom teeth prevents the mouth from closing completely. This is because the wearer's top teeth are separated from the wearer's bottom teeth by the respective first wedge portion 13 and second wedge portion 15. As a result, an air passageway is provided between the wedged apart top and bottom teeth. The bridge member 17 serves to keep the first wedge portion 13 and the second wedge portion 15 in proper orientation with respect to each other, and the bridge member 17 rises out of the way of the user's tongue so that the user's tongue can rest under the bridge member 17.

Substantial pressure can be maintained between the lower jaw and the upper jaw of the wearer by the first wedge portion 13 and the second wedge portion 15 as the air channel is provided without placing a strain on jaw muscles. Therefore, a wearer using the invention can readily maintain one's head in a proper orientation for a CAT test without moving due to strain of jaw muscles.

The mouthpiece with a breathing channel of the invention can also be used by persons, such as athletes, who have trouble breathing through their noses.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved mouthpiece with a breathing channel that is low in cost, relatively simple in design and operation, and which may advantageously be used to permit a wearer's tongue to be maintained in its natural position in the mouth when the mouthpiece is worn. With the invention, a mouthpiece with a breathing channel is provided which does not shift the jaw to an unnatural position when the mouthpiece is in use. With the invention, a mouthpiece with a breathing channel is provided which does not include superfluous components for connecting to mouth-held implements. With the invention, a mouthpiece with a breathing channel is provided which does not include a handle for positioning the mouthpiece in the mouth. With the invention, a mouthpiece with a breathing channel is provided which can be fitted to the respective shapes and sizes of a wearer's teeth. With the invention, a mouthpiece with a breathing channel is provided which affords a wearer an opportunity to allow the lower jaw to be pressed up against the upper jaw without straining jaw muscles and without causing head movement.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and descried in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by letters patent of the United States is as follows:

1. A new and improved mouthpiece apparatus which includes a breathing channel, said apparatus comprising:

a first wedge portion for wedging between top teeth and bottom teeth of a first side of a wearer's mouth, wherein said first wedge portion includes a proximal end and a distal end, a second wedge portion for wedging between top teeth and bottom teeth of a second side of a wearer's mouth, wherein said second wedge portion includes a proximal end and a distal end, and a bridge member connecting said first wedge portion to said second wedge portion, wherein said bridge member is an inverted U-shaped rod structure that has two ends, wherein a first end of said U-shaped bridge member structure is connected to said proximal end of said first wedge portion, and wherein a second end of said U-shaped bridge member structure is connected to said proximal end of said second wedge portion, wherein said first wedge portion and said second wedge portion lie in a common plane, and wherein said bridge member projects outward from said common plane toward said respective distal ends of said first wedge portion and said second wedge portion, such that a wearer's tongue can be located under said bridge member.

2. The apparatus described in claim 1 wherein said first wedge portion and said second wedge portion are approximately quarter-circular structures, such that an overall profile of said first wedge portion, said bridge member, and said second wedge portion is semi-circular.

* * * * *